United States Patent
Van Lancker et al.

(10) Patent No.: US 11,369,138 B2
(45) Date of Patent: Jun. 28, 2022

(54) DIRT-REPELLENT, HEAT-REFLECTIVE COATING FOR AEROSOL-GENERATING DEVICE

(71) Applicant: Philip Morris Products S.A., Neuchatel (CH)

(72) Inventors: Pieter Van Lancker, Kortrijk (BE); Louis-Philippe Vancraeynest, Kortrijk (BE); Simon Desnerck, Kortrijk (BE)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 17/252,029

(22) PCT Filed: Jun. 13, 2019

(86) PCT No.: PCT/EP2019/065477
§ 371 (c)(1),
(2) Date: Dec. 14, 2020

(87) PCT Pub. No.: WO2019/238815
PCT Pub. Date: Dec. 19, 2019

(65) Prior Publication Data
US 2021/0259312 A1    Aug. 26, 2021

(30) Foreign Application Priority Data
Jun. 15, 2018   (EP) .................... 18178081

(51) Int. Cl.
*A24F 40/70* (2020.01)
*A24F 40/40* (2020.01)
(Continued)

(52) U.S. Cl.
CPC ............... *A24F 1/20* (2013.01); *A24F 40/40* (2020.01); *A24F 40/42* (2020.01); *A24F 40/46* (2020.01);
(Continued)

(58) Field of Classification Search
CPC .......... A24F 40/40; A24F 40/42; A24F 40/70; A24F 42/60; A24F 42/80; A24F 47/002–008; A61M 11/042; A61M 15/06
See application file for complete search history.

(56) References Cited

U.S. PATENT DOCUMENTS

| | | |
|---|---|---|
| 4,210,160 A | 7/1980 | Wunsche |
| 9,974,329 B2 | 5/2018 | Buehler et al. |

(Continued)

FOREIGN PATENT DOCUMENTS

| | | |
|---|---|---|
| JP | 7-114973 | 5/1995 |
| JP | 2000-133416 | 5/2000 |

(Continued)

OTHER PUBLICATIONS

Russian Federation Office Action dated Sep. 17, 2021 in Russian Federation Patent Application No. 2021100162/03(00283) (submitting English translation only), 5 pages.

(Continued)

*Primary Examiner* — Matthew P Travers
(74) *Attorney, Agent, or Firm* — Oblon, McClelland, Maier & Neustadt, L.L.P.

(57) ABSTRACT

An aerosol-generating device for generating an inhalable vapor is provided, the aerosol-generating device including: a heating chamber configured to receive an aerosol-generating article, an inner wall of the heating chamber including a coating, the coating including a binder material and metal particles embedded in the binder material or the coating includes a metal alloy, and the coating being configured to be heat-reflective and dirt-repellent. A method for manufacturing an aerosol-generating device to generate an inhalable vapor is also provided.

6 Claims, 3 Drawing Sheets

(51) Int. Cl.
*A24F 40/42* (2020.01)
*A24F 40/20* (2020.01)
*A61M 15/06* (2006.01)
*A24F 1/20* (2006.01)
*A24F 40/46* (2020.01)

(52) U.S. Cl.
CPC .............. *A24F 40/70* (2020.01); *A24F 40/20* (2020.01); *A61M 15/06* (2013.01)

(56) References Cited

U.S. PATENT DOCUMENTS

| | | |
|---|---|---|
| 2014/0314397 A1 | 10/2014 | Alima |
| 2014/0338680 A1 | 11/2014 | Abramov et al. |
| 2016/0255879 A1 | 9/2016 | Paprocki et al. |
| 2016/0338402 A1 | 11/2016 | Buehler et al. |
| 2017/0049153 A1* | 2/2017 | Guo .................... A61M 15/06 |
| 2017/0055580 A1 | 3/2017 | Blandino et al. |
| 2017/0156406 A1 | 6/2017 | Abramov et al. |
| 2017/0156407 A1 | 6/2017 | Abramov et al. |
| 2018/0070640 A1* | 3/2018 | Bessant .................. A24F 40/40 |
| 2018/0271171 A1 | 9/2018 | Abramov et al. |
| 2019/0343179 A1* | 11/2019 | Sur ........................ A24F 40/46 |

FOREIGN PATENT DOCUMENTS

| | | |
|---|---|---|
| JP | 2002-310561 | 10/2002 |
| JP | 2014-56205 | 3/2014 |
| JP | 2015-531601 | 11/2015 |
| JP | 2017-31796 | 2/2017 |
| JP | 2018-57276 | 4/2018 |
| RU | 2 608 289 C2 | 1/2017 |
| RU | 2 611 262 C2 | 2/2017 |
| SU | 833623 A1 | 5/1981 |
| WO | WO 2013/034460 A1 | 3/2013 |
| WO | WO 2015/062983 A2 | 5/2015 |
| WO | WO 2016/124550 A1 | 8/2016 |

OTHER PUBLICATIONS

International Search Report and Written Opinion dated Sep. 12, 2019 in PCT/EP2019/065477 filed on Jun. 13, 2019.

Combined Russian Office Action and Search Report dated Jul. 5, 2021 in Russian Application No. 2021100162 (submitting English translation only), 6 pages.

Japanese Office Action dated Feb. 7, 2022 in corresponding Japanese Patent Application No. 2021-517530 (English translation only), 8 pages.

* cited by examiner

DIRT-REPELLENT, HEAT-REFLECTIVE COATING FOR AEROSOL-GENERATING DEVICE

The present invention relates to an aerosol-generating device for generating an inhalable aerosol. Aerosol-generating devices are known which heat but not burn aerosol-generating substrate such as tobacco. These devices heat aerosol-generating substrate to a sufficiently high temperature for creating an aerosol for inhalation by the user.

These aerosol-generating devices typically comprise a heating chamber, wherein a heating element is arranged within the heating chamber. An aerosol-generating article comprising aerosol-generating substrate can be inserted into the heating chamber and heated by the heating element. The heating element is typically configured as a heating pin and penetrates into the aerosol-generating substrate of the aerosol-generating article when the article is inserted into the heating chamber. Such aerosol-generating devices are typically powered by sources with finite energy capacity, such as batteries. Conventional aerosol-generating devices also have a restricted size and weight as they tend to be portable. Hence, the operating time of such aerosol-generating devices is typically limited by the battery capacity within the size constraints of the design. Typically, the operating time is further reduced by heat loss from the heating chamber during operation.

Thus, in order to maximize the operating time of such aerosol generating devices, there is a need for reducing heat loss.

Frequently, aerosols generated by such aerosol-generating devices condense on the inner wall of the heating chamber. Residues of aerosol-generating substrate may stick to the inner wall of the heating chamber. This can lead to undesirable deposits of aerosol-generating substrate on the inner wall of the heating chamber.

Hence, it is also desirable to provide an aerosol generating device which is less prone to formation of deposits of aerosol-generating substrate and easier to clean.

For solving this and further objects, the present invention proposes an aerosol-generating device for generating an inhalable vapor. The aerosol-generating device comprises a heating chamber configured to receive an aerosol-generating article. The inner wall of the heating chamber comprises a coating. The coating comprises a binder material and metal particles embedded in the binder material. Alternatively, the coating comprises a metal alloy. The coating may be configured to be heat-reflective and dirt-repellent.

By providing a heating chamber of an aerosol-generating device with a heat-reflective and dirt-repellent coating, several features of the aerosol-generating device may be improved. During operation, aerosol deposits may adhere to the walls of the heating chamber. The dirt-repellent characteristic of the coating may prevent or reduce unwanted residues on the coating surface. Also, the efficiency of cleaning of the heating chamber may be increased, as deposits will not strongly adhere to the dirt-repellent surface. Therefore, the heat-reflective characteristics of the coating will last longer, since the coating will not get covered by unwanted residues.

Due to the heat-reflective characteristic of the coating, radiation generated by the device is reflected more efficiently within the chamber. Hence, heat loss is reduced during operation of the device. Furthermore, the reflection of the radiation within the chamber will allow for more even heat distribution in the aerosol-generating article. This may lead to a faster heat-up time and more efficient heating as well as less energy consumption.

The heat-reflective and dirt-repellent coating may comprise a binder material and metal particles embedded in the binder material. The binder material may line the inner wall of the heating chamber. The metal particles are substantially surrounded by the binder material. The binder material fixes the position of the metal particles relative to each other, to the inner wall of the heating chamber and to the binder material. The binder material adheres to the inner wall of the heating chamber.

The inner wall of the heating chamber is preferably the wall enclosing the outer circumference of the heating chamber. The heating chamber preferably has a cylindrical shape. The heating chamber preferably has a hollow tubular shape. The heating chamber preferably has a base. The base may be part of the inner wall. The heating chamber preferably has an opening, into which an aerosol-generating article can be inserted. The opening preferably is not part of the inner wall.

The dirt-repellent and heat-reflective coating may be applied to the inner wall of the heating chamber, for instance, by vapor deposition, thermal spraying, plasma spraying, physical or chemical vapor deposition, electroplating, multilayer deposition process, powder coating, dip coating or film coating processes. Providing the dirt-repellent and heat-reflective material as a coating facilitates ease of application of the material. During manufacturing, the coating may be applied to the sidewall of the heating chamber.

Preferably, the heat-reflective and dirt-repellent coating of the inner wall of the heating chamber of the aerosol-generating device consists of a binder material and metal particles embedded in the binder material or the coating consists of a metal alloy.

The heat-reflective and dirt-repellent coating may comprise a surface nanostructure. The nanostructure provides the surface with an increased surface roughness in comparison with a surface lacking such a nanostructure. The nanostructure may lead to enhanced hydrophobicity of the surface, indicated, for instance, by increased contact angle values. The nanostructure can be achieved by adding nanoparticles to the binder material or combining the binder material with a textured surface, followed by chemical modification. Furthermore, the nanostructure can be achieved, for instance, by the addition of glass fluxes, nanoparticle adhesion, sol-gel processing, hot end float process, thermal plasma spray, bio-engineered self-assembly (diatom growth) or etching. The enhanced hydrophobicity of the coating resulting from the nanostructure is indicative of enhanced cleaning efficiency and reduced deposition of aerosol-generation substrate on the surface.

The binder material of the heat-reflective and dirt-repellent coating may be a polymeric material or an enamel frit. Preferably, such polymeric material has a low surface tension of for example less than 40 millinewton per meter at 20° C. Coatings possessing a lower surface tension have a higher hydrophobicity.

Preferably, the polymeric material comprises acrylic, amide, imide, carbonate, diene, polyester, ether, fluorocarbon, olefin, styrene, vinyl acetal, vinyl chloride, vinylidene chloride, vinyl ester, vinyl ether, vinyl ketone, vinyl pyridine and vinylpyrrolidione polymers.

The binder may comprise an opaque polymer or enamel material, if the metal particles are arranged on or near the surface of the binder facing the inner of the heating chamber. The term "near" specifies that more than 50%, preferably more than 70%, more preferably more than 90% of the metal particles are arranged closer to the surface of the coating facing the inner of the heating chamber than the surface of the coating facing the inner wall of the heating chamber.

The binder may be configured thermally stable such that melting of the binder is prevented during operation of the heating element.

The dirt-repellent and heat-reflective coating may be configured to at least partly reflect infrared radiation. The metal particles of the heat-reflective and dirt-repellent coating may comprise a metal selected from the group of aluminum, copper, gold, silver, alloys thereof or combinations thereof. Alternatively, metal oxide particles, such as oxides of titanium, iron, cobalt and mixtures thereof, can be used. Other metals reflecting infrared radiation may be employed. Preferably, the particles are positioned on or near the surface of the heat reflective coating facing the inner of the heating chamber to increase radiation reflection efficiency. If desired, the metal particles may comprise particles which absorb infrared radiation so that the infrared radiation is converted into heat within the coating migrated through the coating by means of conduction.

The heat-reflective and dirt-repellent coating may be configured scratch resistant to prevent damage to the coating during insertion and removal of an aerosol-generating article.

The heat-reflective and dirt-repellent coating may comprise a metal alloy with non-stick properties. Examples of such metal alloys are boron-aluminum-magnesium, nickel-chrome-chromic carbide, nickel-aluminum-molybdenum, aluminum-copper-iron, aluminum-copper-iron-chromium as well as titanium and chromium based alloys. The coating may comprise multiple layers of metal alloys. Preferably, the coating comprises a single layer of nickel-aluminum-molybdenum. Alternatively, the coating may comprise a layer of nickel-chrome-chromic carbide and a layer of nickel-aluminum-molybdenum. The layer of nickel-aluminum-molybdenum may line the inner wall of the heating chamber and the nickel-chrome-chromic carbide layer may line the layer nickel-aluminum-molybdenum, such that the nickel-chrome-chromic carbide layer faces the inner of the heating chamber. The coating may comprise multiple layers consisting of titanium and chromium based alloys. The coating may comprise a layer of a quasi-crystal structure comprising aluminum-copper-iron (Al—Cu—Fe) or aluminum-copper-iron-chromium (Al—Cu—Fe—Cr) alloy.

The heating element may be arranged centrally aligned along the longitudinal axis of the heating chamber. The heating element may be configured as a pin or blade. The pin or blade is configured to penetrate into the aerosol-generating substrate of an aerosol-generating article during insertion of the aerosol-generating article into the heating chamber. The heating element may also be provided as an external heater surrounding the heating chamber.

The aerosol-generating device may comprise further components such as a control element and a battery. The battery may be configured to supply electric power to the heating element for operating the heating element. The control element may be configured to control the flow of electrical energy from the battery towards the heating element.

The invention also relates to a method for manufacturing an aerosol-generating device to generate an inhalable vapor, wherein the method comprises the following steps:
  i. providing a heating chamber configured to receive an aerosol-generating article,
  ii. applying a coating to the inner wall of the heating chamber, wherein the coating comprises a binder material and metal particles embedded in the binder material or the coating comprises a metal alloy, and wherein the coating may be configured to be heat-reflective and dirt-repellent.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article.

As used herein, the terms 'aerosol-generating article' refer to an article comprising an aerosol-forming substrate that is capable of releasing volatile compounds that can form an aerosol. For example, an aerosol-generating article may be a smoking article that generates an aerosol that is directly inhalable into a user's lungs through the user's mouth. An aerosol-generating article may be disposable. A smoking article comprising an aerosol-forming substrate comprising tobacco is referred to as a tobacco stick.

The portion of the heating element, which is in contact with the aerosol-forming substrate is heated as a result of electrical current passing through the heating element. The current is supplied by a battery. In one embodiment, this portion of the heating element is configured to reach a temperature of between about 300° C. and about 550° C. in use. Preferably, the heating element is configured to reach a temperature of between about 320° C. and about 350° C.

As used herein, an 'aerosol-generating device' relates to a device that interacts with an aerosol-forming substrate to generate an aerosol. The aerosol-forming substrate may be part of an aerosol-generating article, for example part of a smoking article. An aerosol-generating device may be a smoking device that interacts with an aerosol-forming substrate of an aerosol-generating article to generate an aerosol that is directly inhalable into a user's lungs thorough the user's mouth. An aerosol-generating device may be a holder.

The device is preferably a portable or handheld device that is comfortable to hold between the fingers of a single hand. The device may be substantially cylindrical in shape and has a length of between 70 and 120 mm. The maximum diameter of the device is preferably between 10 and 20 mm. In one embodiment the device has a polygonal cross section and has a protruding button formed on one face. In this embodiment, the diameter of the device is between 12.7 and 13.65 mm taken from a flat face to an opposing flat face; between 13.4 and 14.2 taken from an edge to an opposing edge (i.e., from the intersection of two faces on one side of the device to a corresponding intersection on the other side), and between 14.2 and 15 mm taken from a top of the button to an opposing bottom flat face.

The device may be an electrically heated smoking device.

The device may include other heaters. For example the device may include an external heater positioned around a perimeter of the cavity. An external heater may take any suitable form. For example, an external heater may take the form of one or more flexible heating foils on a dielectric substrate, such as polyimide. The flexible heating foils can be shaped to conform to the perimeter of the cavity. Alternatively, an external heater may take the form of a metallic grid or grids, a flexible printed circuit board, a moulded interconnect device (MID), ceramic heater, flexible carbon fibre heater or may be formed using a coating technique, such as plasma vapour deposition, on a suitable shaped substrate. An external heater may also be formed using a metal having a defined relationship between temperature and resistivity. In such an exemplary device, the metal may be formed as a track between two layers of suitable insulating materials. An external heater formed in this manner may be used to both heat and monitor the temperature of the external heater during operation.

The power supply may be any suitable power supply, for example a DC voltage source such as a battery. In one embodiment, the power supply is a Lithium-ion battery. Alternatively, the power supply may be a Nickel-metal hydride battery, a Nickel cadmium battery, or a Lithium based battery, for example a Lithium-Cobalt, a Lithium-Iron-Phosphate, Lithium Titanate or a Lithium-Polymer battery.

The control element may be a simple switch. Alternatively the control element may be electric circuitry and may comprise one or more microprocessors or microcontrollers.

In another aspect of the invention, there is provided an aerosol-generating system comprising an aerosol-generating device according to the description above and one or more aerosol-forming articles configured to be received in the cavity of the aerosol-generating device.

During operation an aerosol-generating article containing the aerosol-forming substrate may be partially contained within the aerosol-generating device.

The aerosol-generating article may be substantially cylindrical in shape. The aerosol-generating article may be substantially elongate. The aerosol-generating article may have a length and a circumference substantially perpendicular to the length. The aerosol-forming substrate may be substantially cylindrical in shape. The aerosol-forming substrate may be substantially elongate. The aerosol-forming substrate may also have a length and a circumference substantially perpendicular to the length.

The aerosol-generating article may have a total length between approximately 30 mm and approximately 100 mm. The aerosol-generating article may have an external diameter between approximately 5 mm and approximately 12 mm. The aerosol-generating article may comprise a filter plug. The filter plug may be located at a downstream end of the aerosol-generating article. The filter plug may be a cellulose acetate filter plug. The filter plug is approximately 7 mm in length in one embodiment, but may have a length of between approximately 5 mm to approximately 10 mm.

In one embodiment, the aerosol-generating article has a total length of approximately 45 mm. The aerosol-generating article may have an external diameter of approximately 7.2 mm. Further, the aerosol-forming substrate may have a length of approximately 10 mm. Alternatively, the aerosol-forming substrate may have a length of approximately 12 mm. Further, the diameter of the aerosol-forming substrate may be between approximately 5 mm and approximately 12 mm. The aerosol-generating article may comprise an outer paper wrapper. Further, the aerosol-generating article may comprise a separation between the aerosol-forming substrate and the filter plug. The separation may be approximately 18 mm, but may be in the range of approximately 5 mm to approximately 25 mm.

The aerosol-forming substrate may be a solid aerosol-forming substrate. Alternatively, the aerosol-forming substrate may comprise both solid and liquid components. The aerosol-forming substrate may comprise a tobacco-containing material containing volatile tobacco flavour compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

If the aerosol-forming substrate is a solid aerosol-forming substrate, the solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco, cast leaf tobacco and expanded tobacco. The solid aerosol-forming substrate may be in loose form, or may be provided in a suitable container or cartridge. Optionally, the solid aerosol-forming substrate may contain additional tobacco or non-tobacco volatile flavour compounds, to be released upon heating of the substrate. The solid aerosol-forming substrate may also contain capsules that, for example, include the additional tobacco or non-tobacco volatile flavour compounds and such capsules may melt during heating of the solid aerosol-forming substrate.

As used herein, homogenised tobacco refers to material formed by agglomerating particulate tobacco. Homogenised tobacco may be in the form of a sheet. Homogenised tobacco material may have an aerosol-former content of greater than 5% on a dry weight basis. Homogenised tobacco material may alternatively have an aerosol former content of between 5% and 30% by weight on a dry weight basis. Sheets of homogenised tobacco material may be formed by agglomerating particulate tobacco obtained by grinding or otherwise combining one or both of tobacco leaf lamina and tobacco leaf stems. Alternatively, or in addition, sheets of homogenised tobacco material may comprise one or more of tobacco dust, tobacco fines and other particulate tobacco by-products formed during, for example, the treating, handling and shipping of tobacco. Sheets of homogenised tobacco material may comprise one or more intrinsic binders, that is tobacco endogenous binders, one or more extrinsic binders, that is tobacco exogenous binders, or a combination thereof to help agglomerate the particulate tobacco; alternatively, or in addition, sheets of homogenised tobacco material may comprise other additives including, but not limited to, tobacco and non-tobacco fibres, aerosol-formers, humectants, plasticisers, flavourants, fillers, aqueous and non-aqueous solvents and combinations thereof.

Optionally, the solid aerosol-forming substrate may be provided on or embedded in a thermally stable carrier. The carrier may take the form of powder, granules, pellets, shreds, spaghettis, strips or sheets. Alternatively, the carrier may be a tubular carrier having a thin layer of the solid substrate deposited on its inner surface, or on its outer surface, or on both its inner and outer surfaces. Such a tubular carrier may be formed of, for example, a paper, or paper like material, a non-woven carbon fibre mat, a low mass open mesh metallic screen, or a perforated metallic foil or any other thermally stable polymer matrix.

In a particularly preferred embodiment, the aerosol-forming substrate comprises a gathered crimpled sheet of homogenised tobacco material. As used herein, the term 'crimped sheet' denotes a sheet having a plurality of substantially parallel ridges or corrugations. Preferably, when the aerosol-generating article has been assembled, the substantially parallel ridges or corrugations extend along or parallel to the longitudinal axis of the aerosol-generating article. This advantageously facilitates gathering of the crimped sheet of homogenised tobacco material to form the aerosol-forming substrate. However, it will be appreciated that crimped sheets of homogenised tobacco material for inclusion in the aerosol-generating article may alternatively or in addition have a plurality of substantially parallel ridges or corrugations that are disposed at an acute or obtuse angle to the longitudinal axis of the aerosol-generating article when the aerosol-generating article has been assembled. In certain embodiments, the aerosol-forming substrate may comprise a gathered sheet of homogenised tobacco material that is substantially evenly textured over substantially its entire surface. For example, the aerosol-forming substrate may comprise a gathered crimped sheet of homogenised tobacco material comprising a plurality of substantially parallel ridges or corrugations that are substantially evenly spaced-apart across the width of the sheet.

The solid aerosol-forming substrate may be deposited on the surface of the carrier in the form of, for example, a sheet, foam, gel or slurry. The solid aerosol-forming substrate may be deposited on the entire surface of the carrier, or alternatively, may be deposited in a pattern in order to provide a non-uniform flavour delivery during use.

An aerosol-generating system is a combination of an aerosol-generating device and one or more aerosol-generating articles for use with the device. However, the aerosol-generating system may include additional components, such as for example a charging unit for recharging an on-board electric power supply in an electrically operated or electric aerosol-generating device The invention will be further described, by way of example only, with reference to the accompanying drawings in which.

Figure 1:
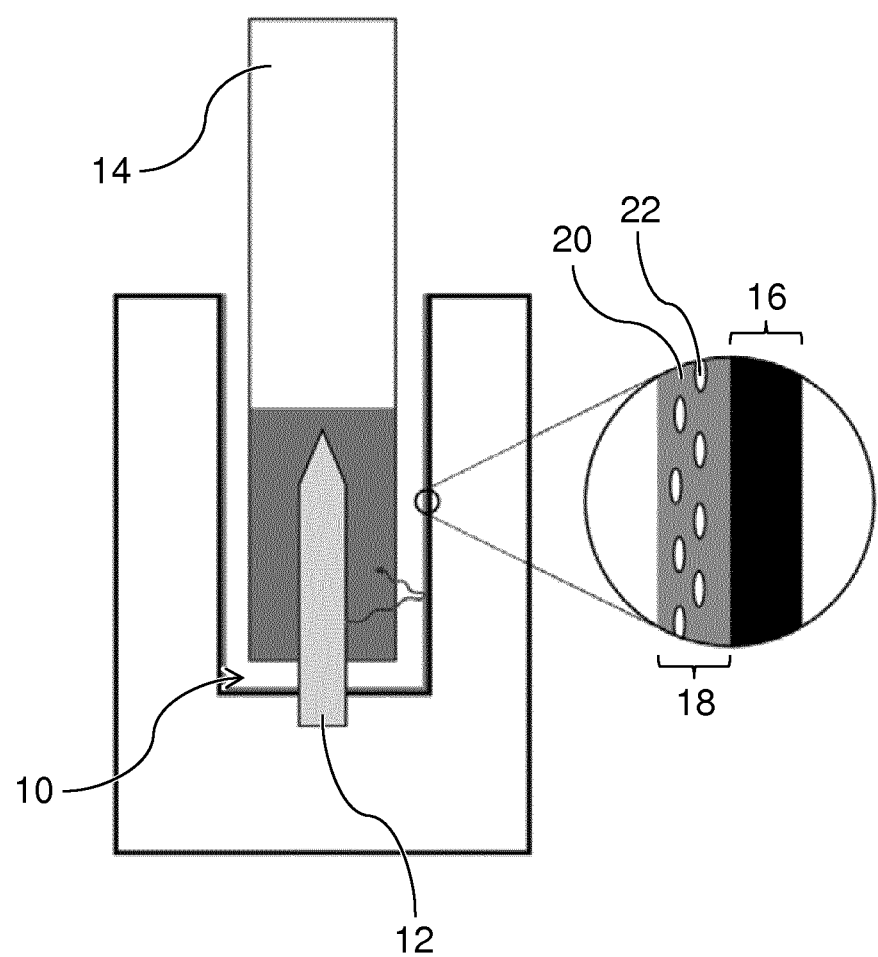
FIG. 1 shows a cross-sectional view of a heating chamber of an aerosol-generating device according to the invention with a coating comprising a binder material and metal particles.

FIG. 1 shows a cross-sectional view of a heating chamber 10 of an aerosol-generating device according to the invention. An aerosol-generating article 14 containing aerosol-generating substrate is inserted in the heating chamber 10. A blade-shaped heating element 12 penetrates into the aerosol-generating article 14. The inner wall 16 of the heating chamber 10 is lined with a dirt-repellent and heat-reflective coating 18. The coating 18 comprises a binder material 20 and metal particles 22 embedded within the binder material 20. The binder material 20 may comprise a polymeric material or an enamel frit.

The heating element 12 is configured for heating the aerosol-generating substrate contained in the aerosol-generating article 14 for generating an inhalable aerosol. The dirt-repellent and heat-reflective coating 18 at least partially reflects the heat radiated by the heating element 12 and not fully absorbed by the aerosol-generating article 14. The heat is thus at least partly reflected back from the inner wall 16 of the heating chamber 10 towards the aerosol-generating article 14.

The dirt-repellent and heat-reflective coating 18 is configured to reduce or prevent residues of the aerosol-generating substrate from adhering to the inner wall 16 of the heating chamber 10. Particularly during insertion and removal of aerosol-generating articles 14, formation of substrate residues on the surface of the inner wall 16 are reduced.

Figure 2:
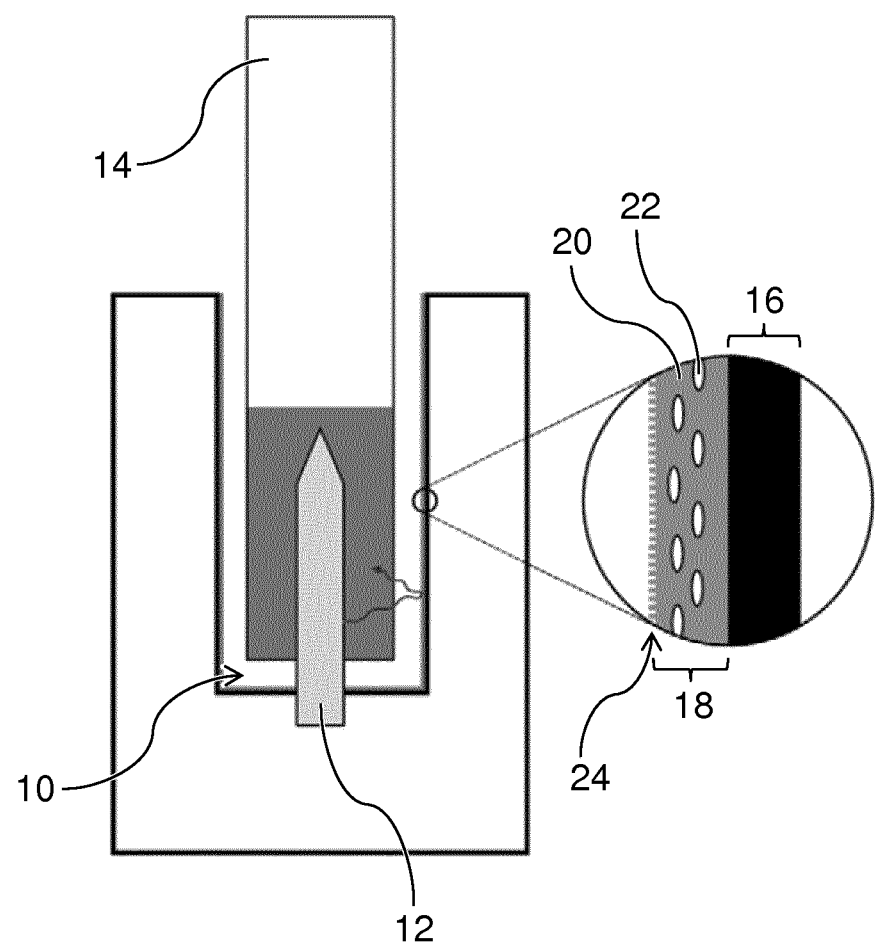
FIG. 2 shows a cross-sectional view of a heating chamber of the aerosol-generating device, in which the coating comprises a surface nanostructure.

FIG. 2 shows a surface nanostructure 24 of the dirt-repellent and heat-reflective coating 18 lining the heating chamber 10. The surface nanostructure 24 enhances the hydrophobicity of the coating. The surface nanostructure 24 is configured to reduce adherence of residues of aerosol-generating substrate to the surface of the inner wall 16 of the heating chamber 10. The surface nanostructure 24 has the shape of nanoprotrusions on the surface of the dirt-repellent and heat-reflective coating 18.

Figure 3:
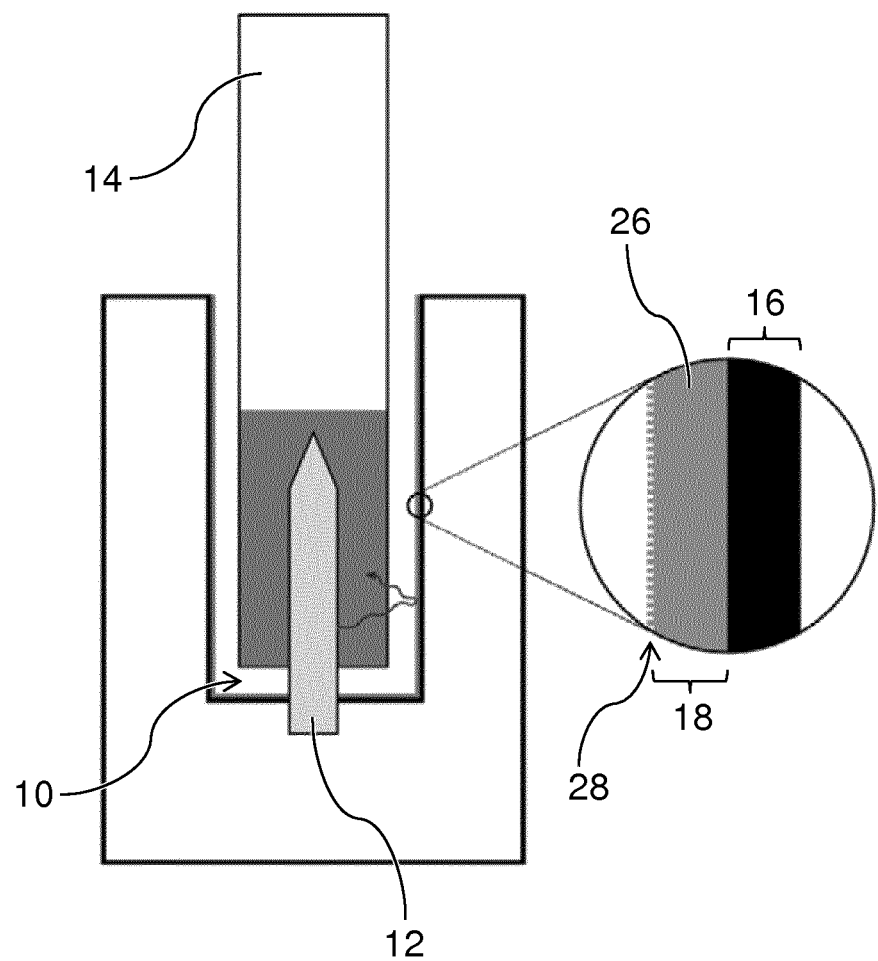
FIG. 3 shows a cross-sectional view of the heating chamber of the aerosol-generating device, in which the coating consists of a metal alloy.

FIG. 3 shows the dirt-repellent and heat-reflective coating 18 consisting of a metal alloy 26. The metal alloy 26 comprises a surface nanostructure 28 on the surface of the coating 18 facing the inner of the heating chamber 10. The surface nanostructure 28 increases the hydrophobicity of the coating 18 such that the coating possesses enhanced dirt-repellent properties.

The invention claimed is:

1. An aerosol-generating device for generating an inhalable vapor, the aerosol-generating device comprising:
a heating chamber configured to receive an aerosol-generating article,
wherein an inner wall of the heating chamber comprises a coating,
wherein the coating comprises a binder material and metal particles embedded in the binder material, and
wherein the binder material is configured as an enamel frit.

2. The aerosol-generating device according to claim 1, wherein the coating consists of the binder material and metal particles embedded in the binder material.

3. The aerosol-generating device according to claim 1,
wherein the coating further comprises a nanostructure on a surface of the coating facing the interior of the heating chamber, and
wherein the nanostructure is configured to increase a hydrophobicity of the surface.

4. The aerosol-generating device according to claim 1, wherein the metal particles comprise one or more of aluminum, copper, gold, silver, or alloys thereof.

5. The aerosol-generating device according to claim 1, wherein the metal particles are disposed near a surface of the coating facing the interior of the heating chamber.

6. A method for manufacturing an aerosol-generating device to generate an inhalable vapor, the method comprising the following steps:
i) providing a heating chamber configured to receive an aerosol-generating article; and
ii) applying a coating to an inner wall of the heating chamber,
wherein the coating comprises a binder material and metal particles embedded in the binder material, and
wherein the binder material is configured as an enamel frit.

* * * * *